United States Patent [19]

Yang et al.

[11] Patent Number: 5,994,566

[45] Date of Patent: Nov. 30, 1999

[54] PROCESS FOR PREPARING 6(R)-2 (8-HYDROXY-2,6-DIMETHYL-POLYHYDRO-NAPHTHYL-1)-4-(R)-HYDROXY-3,4,5,6-TETRAHYDRO-2H-PYRAN-2-ONE

[75] Inventors: Yuh-Lin Yang, Hsinchu-Hsien; Yeuk-Chuen Liu, Hsinchu, both of Taiwan

[73] Assignees: Industrial Technology Research Institute, Hsinchu, Taiwan; Yung Shin Pharmaceutical Ind. Co., Ltd., Taichung Hsien, Taiwan

[21] Appl. No.: 09/106,277

[22] Filed: Jun. 29, 1998

[51] Int. Cl.$^6$ .................................................. C07D 309/30
[52] U.S. Cl. ............................................................ 549/292
[58] Field of Search ............................................... 549/292

[56] References Cited

U.S. PATENT DOCUMENTS 4,293,496 10/1981 Williard .................................. 424/279
4,444,784 4/1984 Hoffman et al. ........................ 549/292

*Primary Examiner*—Amelia Owens
*Attorney, Agent, or Firm*—Sughrue, Mion, Zinn, Macpeak & Seas, PLLC

[57] ABSTRACT

The process for preparing compound 2 by reacting the compound 1, each as described in the specification hereof, with a tetraalkyl ammonium hydroxide having the formula $R_1R_2R_3R_4N^+OH^-$, wherein $R_1$, $R_2$, $R_3$ and $R_4$ are each independently a $C_1$–$C_{10}$ alkyl group or a ($C_6$–$C_{10}$) aryl ($C_1$–$C_{10}$) alkyl group, to obtain an triol carboxylate thereof, acidifying the triol carboxylate, then lactonizing the product to obtain diol lactone, a key intermediate for production of antihypercholesterolemia agents.

14 Claims, No Drawings

PROCESS FOR PREPARING 6(R)-2 (8-HYDROXY-2,6-DIMETHYL-POLYHYDRO-NAPHTHYL-1)-4-(R)-HYDROXY-3,4,5,6-TETRAHYDRO-2H-PYRAN-2-ONE

BACKGROUND OF THE INVENTION

1. Field of the Invention

The present invention in general relates to a process for preparing an intermediate of an antihypercholestero-lemia agent, and in particular to a process for preparing compound 2 from compound 1, each as described below, by using tetraalkyl ammonium hydroxide as a hydrolytic reagent.

2. Description of the Related Art

Antihypercholesterolemia agents such as Simvastatin (compound 6), 6(R)-{2-8'(S)-2",2"-dimethylbutyryloxy-2'(S)-6'(R)-dimethyl-1',2',6',7',8'8'a(R)-hexahydronapthyl-1'(S)-ethyl}-4(R)-hydroxy-3,4,5,6-tetrahydro-2H-pyran-2-one are strong inhibitors of the biosynthesis of cholesterol. Simvastatin is prepared from the starting material lovastatin (compound 1). The 8'-ester group on the polyhydronaphthyl ring of the starting material, lovastatin 1, is first hydrolyzed to form 8'-hydroxy compound 2. The 4-hydroxyl group on the lactone ring of the 8'-hydroxy compound 2 is then protected with t-butyldimethylchlorosilane in an inert atmosphere at room temperature (about 20–30° C.) in the presence of an acid acceptor such as imidazole to form a β-hydroxy protected derivative 3. The 8'-hydroxy on the polyhydronaphthyl ring of the compound 3 is then acylated in one of two methods. The first method comprises treatment with the acid chloride of the desired acyl group in pyridine with 4,4-dimethylaminopyridine as catalyst. The second method comprises treatment of the 8'-polyhydronaphthol with the free acid of the desired acyl group and an N',N'-dicyclohexylcarbodimide with 4-pyrrolidinopyridine as a catalyst in dichloromethane. These procedures give the protected ester, compound 4. The removal of the silyl protecting group from the 4-hydroxy group of the lactone ring is then carried out, using three equivalents of tetrabutylammonium fluoride and four equivalents of acetic acid per equivalent of the ester to give the desired compound 6, simvastatin. The reaction scheme of the above process is indicated below.

REACTION SCHEME

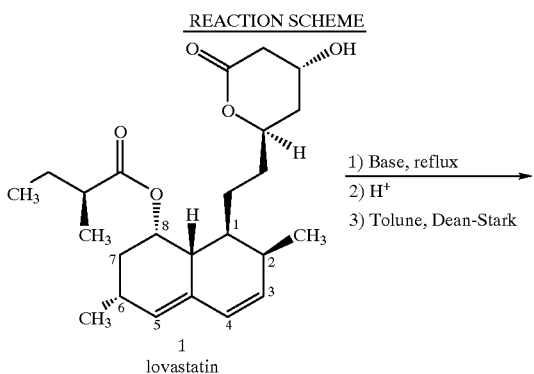

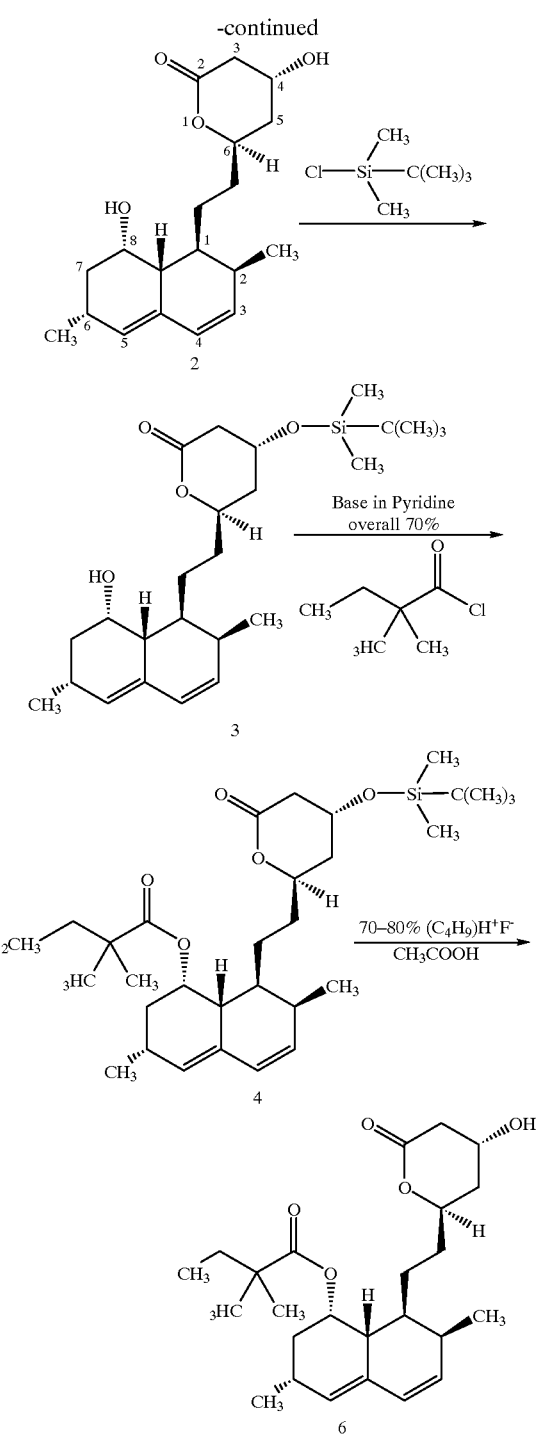

U.S. Pat. Nos. 4,293,496 and 4,444,784 disclose a process for preparing compound 2 from compound 1. The process includes heating lovastatin with an alkali metal hydroxide, such as lithium hydroxide, potassium hydroxide or sodium hydroxide, in a protoic solvent such as water or an alcohol followed by acidification and lactonization. Although the α-methylbutyryl ester of lovastatin is highly sterically hindered, employing strong base such as sodium hydroxide or potassium hydroxide for hydrolysis is disadvantageous because the base-sensitive β-hydroxy lactone group tends to form eliminated side product extensively under this condition. Thus, in industrial applications, the weak nucleophilic base, lithium hydroxide, is used for the hydrolysis process. However, when lithium hydroxide is used, the hydrolysis process must be performed at an elevated temperature, for example 120° C.–180° C., for an extended period, (longer than 72 hours), and the yield after acidification and lactonization is not high, i.e. less than 80%. Moreover, lithium hydroxide can easily react with trace amounts of carbon dioxide in the reaction system and precipitate out as lithium carbonate. The precipitate will hinder the further work-up process.

SUMMARY OF THE INVENTION

It is thereof an object of the invention to provide a process of preparing compound 2, of eliminating the disadvantages of the conventional process.

The object of the invention is attained by using tetraalkyl ammonium hydroxide as a hydrolysis agent. The process of the invention can be completed within 8 hours achieving a yield of higher than 90% with no precipitates formed.

Specifically, the process of the invention includes reacting a compound having a formula (I)

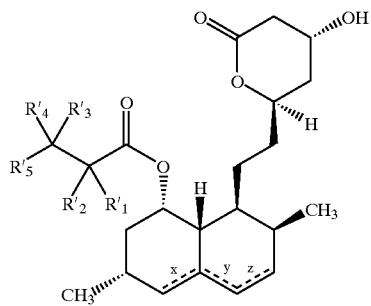
(I)

wherein the dotted lines, x, y and z represent possible double bonds, said double bonds, when any are present, being either x and z in combination or one of x, y, z alone, and $R'_1$, $R'_2$, $R'_3$, $R'_4$ and $R'_5$ are each independently, a hydrogen atom or a $C_1$–$C_{10}$ alkyl group;

with a tetraalkyl ammonium hydroxide to obtain a triol carboxylate thereof, followed by acidification and subsequently lactonization to obtain the compound (II) of the following formula:

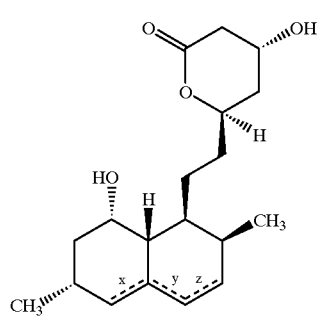
(II)

wherein the dotted lines x, y and z represent possible double bonds, said double bonds, when any are present, being either x and z in combination or one of x, y or z alone.

Other features and advantages of the present invention will be apparent from the following detailed description and examples, and also from the claims.

DETAILED DESCRIPTION OF THE INVENTION

Suitable tetraalkyl ammonium hydroxides useful in the invention are of the formula $R_1R_2R_3R_4NOH$ wherein $R_1$, $R_2$, $R_3$ and $R_4$ are each independently a $C_1$–$C_{10}$ alkyl group or a $(C_6$–$C_{10})$aryl$(C_1$–$C_{10})$ alkyl group. Suitable examples of tetraalkyl ammonium hydroxide include but are not limited to tetrabutyl ammonium hydroxide tetraethyl ammonium hydroxide, tetramethyl ammonium hydroxide, and trimethyl phenylmethyl ammonium hydroxide. The amount of tetraalkyl ammounium hydroxide is 4–10 mole equivalents per 1 mole equivalent of the compound (I), preferably 6 mole equivalents.

The hydrolysis reaction of compound (I) with tetraalkyl ammonium hydroxide is carried out by adding tetraalkyl ammonium hydroxide to an aqueous suspension of the compound (I) and heating the mixture at 100° C.–120° C. with reflux for 4–7 hours.

According to the invention, it is possible during the reacting step to use a portion of strong base such as sodium hydroxide or potassium hydroxide to reduce the consumption of the expensive tetraalkyl ammonium hydroxide. In this case, the tetraalkyl ammonium hydroxide is added to an aqueous suspension of compound (I), then an aqueous solution of a strong base such as sodium or potassium hydroxide is added to this reaction mixture and the mixture is heated to 100° C.–120° C. with reflux for 4–7 hours.

The resulting triol carboxylate is acidified to pH 1–4 by adding an acid such as concentrated hydrochloric acid in ice bath. The acidified reaction mixture is then lactonized in an appropriate organic solvent, such as toluene or benzene, to obtain the product, compound (II). The lactonization step should preferably be carried out for a time period of 45 minutes to 3 hours to avoid the production of β-eliminated side products which affect subsequent isolation and purification.

The following examples are given to illustrate the present invention without limiting its scope. Unless otherwise indicated, all parts, percents, ratios and the like are by weight.

EXAMPLE 1

To a suspension of lovastatin (1.01 g, 2.5 mmole) in water (3 ml), was added tetraethyl ammonium hydroxide (20% aqueous solution, 12 ml, 16.3 mmole) under a nitrogen atmosphere and heated to reflux (110–120° C.) for 15 hours. The reaction mixture was cooled with an ice bath and hydrochloric acid (2N, 8.5 ml) was added to adjust to pH 3–4. The acidified solution was extracted with isopropanol (20 ml) three times. The combined organic solution was washed with brine (50 ml). The organic layer was then dried over anhydrous magnesium sulfate, filtered, and concentrated under reduced pressure. Toluene (50 ml) was then added to the residue, heated to reflux under azeotropic condition with a Dean-stark apparatus for 2 hours. The reaction solution was concentrated under reduced pressure to dryness. n-Hexane (40 ml) and ethyl acetate (0.5 ml) were added to the residue and refluxed for 30 minutes. The resulting solution was then cooled in an ice bath for 30 minutes and filtered. The product (compound 2, 0.72 g, 90%) obtained was a white solid.

Spectral Data $^1$HNMR (CDCl$_3$, 200 MHz), (: 0.87 (d, 3, J=7 Hz, CH$_3$), 1.16 (d, 3, J=7 Hz, CH$_3$), 1.25~2.43 (a series of multiplet), 2.65 (m, 2, pyran C-3H), 4.21 (m, 1, naphthalene C-8H), 4.34 (m, 1, pyran, C-4H), 4.68 (m, 1, pyran C-6H), 5.52 (m, 1, napth C-5H), 5.76 (dd, 1, J=6.1, 9.6 Hz, naphth C-3H), 5.96 (d, 1, J=9.6 Hz, naphth C-4H).

EXAMPLE 2

To a suspension of lovastatin (1.01 g, 2.5 mmole) in water (5 ml), phenylmethyl trimethyl ammonium hydroxide (40% aqueous solution, 5 ml, 11.96 mmole was added. The mixture was then heated to reflux (120° C.) for 10 hours. The reaction mixture was cooled with an ice bath and hydrochloric acid (2N, 7.5 ml) was added to adjust to pH 3–4. The acidified solution was then extracted with isopropanol (20 ml(3). The combined isopropanol solutions were washed with brine (50 ml). The combined organic solution was dried over anhydrous magnesium sulfate, filtered, and concentrated under reduced pressure to dryness. Toluene (50 ml) was then added to the residue, heated to reflux under azeotropic condition with a Dean-stark apparatus for 2 hours. The reaction mixture was concentrated under reduced pressure to dryness. n-Hexane (40 ml, 1% ethyl acetate) was added to the residue and refluxed for 30 minutes. The resulting solution was then cooled in an ice bath for 30 minutes. After filtration, the product (compound 2, 0.66 g, 82%) was obtained as a white solid.

Spectral Data $^1$HNMR (CDCl$_3$, 200 MHz), (: 0.87 (d, 3, J=7 Hz, CH$_3$), 1.16 (d, 3, J=7 Hz, CH$_3$), 1.25~2.43 (a series of multiplet), 2.65 (m, 2, pyran C-3H), 4.21 (m, 1, naphthalene C-8H), 4.34 (m, 1, pyran, C-4H), 4.68 (m, 1, pyran C-6H), 5.52 (m, 1, napth C-5H), 5.76 (dd, 1, J=6.1, 9.6 Hz, naphth C-3H), 5.96 (d, 1, J=9.6 Hz, naphth C-4H).

EXAMPLE 3

To a suspension of lovastatin (9.98 g, 24.7 mmole) in water (30 ml) was added tetrabutyl ammonium hydroxide (40% aqueous solution, 82 ml, 126.4 mmole) under a nitrogen atmosphere at room temperature over a 5 minute period. The reaction mixture was then heated to reflux for 7–8 hours. After the reaction finished, the reaction mixture was cooled with an ice bath, and hydrochloric acid (10 ml) was added to adjust the solution to pH 3. The acidified solution was then extracted with ethyl acetate (100 ml) once and with a mixed solution of ethyl acetate (ml) and ethyl isopropanate (50 ml) three times. The combined organic solution was washed with water (150 ml×3) and brine (50 ml×2). The organic layer was then dried over anhydrous sodium sulfate, and concentrated under reduced pressure to dryness. Toluene (200 ml) was then added to the residue, and the mixture heated to reflux under azeotropic conditions with a Dean-stark apparatus for 2.5 hours. The reaction mixture was concentrated under reduced pressure to dryness. n-Hexane (40 ml, 1% ethyl acetate) was added to the residue and the mixture was refluxed for 1 hour. The resulting solution was then cooled in an ice bath for 30 minutes and filtered. The product (compound 2, 7.743 g, 98%) was obtained as a white solid.

Spectral Data $^1$HNMR (CDCl$_3$, 200 MHz), (: 0.87 (d, 3, J=7 Hz, CH$_3$), 1.16 (d, 3, J=7 Hz, CH$_3$), 1.25~2.43 (a series of multiplet), 2.65 (m, 2, pyran C-3H), 4.21 (m, 1, naphthalene C-8H), 4.34 (m, 1, pyran, C-4H), 4.68 (m, 1, pyran C-6H), 5.52 (m, 1, napth C-5H), 5.76 (dd, 1, J=6.1, 9.6 Hz, naphth C-3H), 5.96 (d, 1, J=9.6 Hz, naphth C-4H).

EXAMPLE 4

To a suspension of lovastatin (100 g, 0.247 mole) in water, no tetrabutyl ammonium hydroxide (40% aqueous solution, 304 ml, 0.456 mole) was added dropwise under a nitrogen atmosphere at room temperature over a period of 5 minutes. After the reaction mixture became clear, an aqueous solution of sodium hydroxide (150 ml, 6.6 M, 0.99 mole) was added to the resulting mixture. The reaction mixture was then gradually heated to 115(C. to reflux for 6.5 hours. After the reaction was finished, ethyl acetate (100 ml) and water (50 ml) were added to the reaction mixture and the mixture was cooled in an ice bath. Hydrochloric acid (3N) was then added to adjust the solution to pH 3–4. The acidified solution was then extracted with ethyl acetate (200 ml) twice. The combined organic solution was washed with brine (300 ml). The combined organic solution was then dried over anhydrous magnesium sulfate, filtered, and concentrated under reduced pressure to dryness. Toluene (800 ml) was added to the residue, and the mixture was heated to reflux (125° C.) under azeotropic conditions with a Dean-stark apparatus for 1 hour. After the reaction had cooled to room temperature, the reaction mixture was washed with brine (300 ml×2) and water (300 ml). The organic solution was dried over anhydrous sodium sulfate, filtered and dried under reduced pressure. n-Hexane (100 ml in 1% ethyl acetate) was added to the residue and the mixture was refluxed for 1 hour. The resulting solution was then cooled and filtered. The product (compound 2, 73.4 g, 92.9%) was obtained as a white solid.

Spectral Data $^1$HNMR (CDCl$_3$, 200 MHz), (: 0.87 (d, 3, J=7 Hz, CH$_3$), 1.16 (d, 3, J=7 Hz, CH$_3$), 1.25~2.43 (a series of multiplet), 2.65 (m, 2, pyran C-3H), 4.21 (m, 1, naphthalene C-8H), 4.34 (m, 1, pyran, C-4H), 4.68 (m, 1, pyran C-6H), 5.52 (m, 1, napth C-5H), 5.76 (dd, 1, J=6.1, 9.6 Hz, naphth C-3H), 5.96 (d, 1, J=9.6 Hz, naphth C-4H).

While the invention has been described in detail and with reference to specific embodiments thereof, it will be apparent, to one skilled in the art that various changes and modifications can be made therein without departing from the spirit and scope thereof.

What is claimed is:

1. A process for preparing a compound having the formula (II),

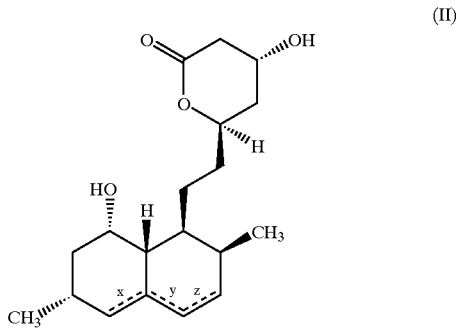

(II)

wherein the dotted lines x, y and z represent possible double bonds, said double bonds, when any are present, being either x and z in combination or one of x, y or z alone, comprising the following steps:

(1) reacting a compound having the formula (I)

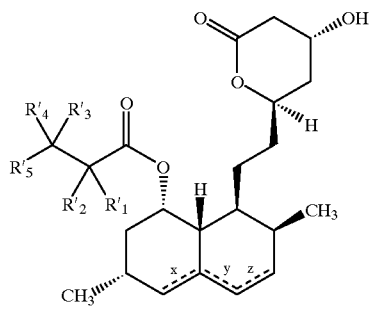

(I)

wherein the dotted lines x, y and z represent possible double bonds, said double bonds, when any are present, being either x and z in combination or one of x, y, z alone, and $R'_1$, $R'_2$, $R'_3$, $R'_4$ and $R'_5$, are each independently a hydrogen atom or a $C_1-C_{10}$ alkyl group;

with a tetraalkyl ammonium hydroxide having the formula $R_1R_2R_3R_4NOH$, wherein $R_1$, $R_2$, $R_3$ and $R_4$ are each independently a $C_1-C_{10}$ alkyl group or a $(C_1-C_{10})$ aryl $(C_6-C_{10})$ alkyl group, to obtain an triol carboxylate thereof;

(2) acidifying said triol carboxylate; and (3) lactonizing said triol carboxylic acid to obtain said compound of formula (II).

2. The process as claimed in claim 1, wherein said reacting step (1) comprises reacting 1 mole equivalent of compound (I) with 4–6 mole equivalents of said tetraalkyl ammonium hydroxide.

3. The process as claimed in claim 1, wherein said reacting step (1) comprises adding said tetraalkyl ammonium hydroxide to a suspension of said compound (I) in water, and heating with reflux.

4. The process as claimed in claim 3, wherein in reacting step (1), the reacting is at a temperature of from 100° C. to 120° C.

5. The process as claimed in claim 1, wherein said tetraalkyl ammonium hydroxide is selected from the group consisting of tetrabutyl ammonium hydroxide, tetraethyl ammonium hydroxide, tetramethyl ammonium hydroxide, and trimethyl phenylmethyl ammonium hydroxide.

6. The process as claimed in claim 5, wherein said tetraalkyl ammonium hydroxide is tetrabutylammonium hydroxide.

7. The process as claimed in claim 5, wherein said tetraalkyl ammonium hydroxide is tetraethyl ammonium hydroxide.

8. The process as claimed in claim 5, wherein said tetraalkyl ammonium hydroxide is tetramethyl ammonium hydroxide.

9. The process as claimed in claim 5, wherein said tetraalkyl ammonium hydroxide is trimethyl phenylmethyl ammonium hydroxide.

10. The process as claimed in claim 1, wherein reacting step comprises:
(a) adding said tetraalkyl ammonium hydroxide to said compound (I) mixture with water to form a mixture,
(b) heating the mixture of (a) to 50° C.–60° C.,
(c) adding an aqueous solution of a alkali metal hydroxide to said mixture of (b), and
(d) heating with reflux.

11. The process as claimed in claim 10, wherein said alkali metal hydroxide is sodium hydroxide.

12. The process as claimed in claim 10, wherein said tetraalkyl ammonium hydroxide and said base are present in a total amount of about 2–6 mole equivalents per mole equivalent of the compound (I) and said alkali metal hydroxide is present in an amount of 0–4 mole equivalents per mole equivalent of the compound (I).

13. The process as claimed in claim 1, wherein said triol carboxylate in step (2) is acidified to pH 1–4.

14. The process as claimed in claim 1, wherein said process comprises lactonizing in step (3) for 45 minutes to 3 hours.

* * * * *